United States Patent [19]

Kamel et al.

[11] Patent Number: 4,919,841

[45] Date of Patent: Apr. 24, 1990

[54] WAX ENCAPSULATED ACTIVES AND EMULSION PROCESS FOR THEIR PRODUCTION

[75] Inventors: Ahmed Kamel, Valley Cottage, N.Y.; Lisa C. Hurckes, Short Hills; Monica M. Morelli, North Arlington, both of N.J.

[73] Assignee: Lever Brothers Company, New York, N.Y.

[21] Appl. No.: 202,853

[22] Filed: Jun. 6, 1988

[51] Int. Cl.[5] .................... B01J 13/02; C07D 251/00; B32B 27/14; C01B 15/00

[52] U.S. Cl. .......................... 252/186.26; 252/186.27; 252/186.3; 252/186.31; 252/186.34; 252/186.35; 252/186.36; 252/186.37; 252/174.13; 427/213.3; 427/213.36; 427/220; 427/221; 428/402.2; 428/402.22; 428/402.24

[58] Field of Search ...................... 252/186.35, 186.34, 252/186.26, 186.27, 186.3, 186.31, 186.36, 186.37; 427/213.3, 213.36; 428/402.2, 402.22, 402.24; 264/4.4

[56] References Cited

U.S. PATENT DOCUMENTS

| | | | |
|---|---|---|---|
| 3,015,128 | 1/1962 | Somerville | 18/2.6 |
| 3,310,612 | 3/1967 | Somerville | 264/4 |
| 3,389,194 | 6/1968 | Somerville | 264/4 |
| 3,847,830 | 11/1974 | Williams et al. | 252/186 |
| 3,856,699 | 12/1974 | Miyano et al. | 427/213.36 X |
| 3,943,063 | 3/1976 | Morishita et al. | 252/316 |
| 4,078,099 | 3/1978 | Mazzola | 427/213 |
| 4,092,285 | 5/1978 | Leo et al. | 260/28.5 |
| 4,136,052 | 1/1979 | Mazzola | 252/94 |
| 4,327,151 | 4/1982 | Mazzola | 428/407 |
| 4,657,784 | 4/1987 | Olson | 427/213 |
| 4,756,844 | 7/1988 | Walles et al. | 252/174.13 X |
| 4,762,637 | 8/1988 | Aronson et al. | 252/186.34 X |

FOREIGN PATENT DOCUMENTS 132184 1/1985 European Pat. Off. .

OTHER PUBLICATIONS

"Chemical Technology", Oct. 1974, pp. 623–626 by Goodwin and Somerville entitled Microencapsulation by Physical Methods.

*Primary Examiner*—Brooks H. Hunt
*Assistant Examiner*—Virginia B. Caress
*Attorney, Agent, or Firm*—Milton L. Honig

[57] ABSTRACT

A process is provided for preparing encapsulated active particles by the steps of: dispersing active materials in molten wax; emulsifying the active/wax dispersion in aqueous surfactant solution for no longer than 4 minutes; quenching the capsules by cooling; and retrieving solidified capsules. The active materials may be selected from chlorine or oxygen bleaching agents, bleach precursors, enzymes, perfumes, fabric softening agents, and surfactants. Optimal capsules are obtainable where a blend of hard and soft waxes are utilized for the coating. The hard and soft waxes are characterized by needle penetration values no higher than 30 mm and no lower than 35 mm, respectively, at 25° C. The resultant capsules have utility for cleaning compositions such as automatic dishwashing detergent formulations.

9 Claims, No Drawings

WAX ENCAPSULATED ACTIVES AND EMULSION PROCESS FOR THEIR PRODUCTION

BACKGROUND OF THE INVENTION

1. Field of the Invention

The invention relates to encapsulated active materials, a process for preparing the encapsulates, and cleaning compositions containing these encapsulates.

2. The Prior Art

Frequently, chemical formulations, especially those in the cleaning arts, contain mutually incompatible components. Problems of this nature have been solved by the use of encapsulation technology. For instance, automatic dishwashing compositions normally include a chlorine bleach. If not protected, perfume, enzyme and surfactants will be attacked by the bleach. Technology exists for encapsulating one or more of the perfume, enzyme or surfactant to insulate these sensitive components from being oxidized. Alternatively, the bleach may be encapsulated within a matrix separating it from the other components.

U.S. Pat. Nos. 4,078,099, 4,136,052 and 4,327,151 all to Mazzola report methods for encapsulating chlorine bleach so that it may be utilized in fabric washing powders without causing fabric color damage. The process involves agitating bleach particles in a mixer and spraying thereonto a mixture of melted fatty acid (melting point 85°–135° F.) and microcrystalline wax (melting point 125°–210° F.). An additional second or third coating may be applied. Each subsequent coating has a slightly different ratio of fatty acid to microcrystalline wax.

EP O No. 132 184 (Scotte) is illustrative of spray technology. The patent describes heating trichloroisocyanuric acid at 50° C. under agitation in a rotary mixer. Polyethylene waxes of melting point below 70° C. are sprayed into the mixer to coat the trichloroisocyanuric acid. The resultant bleach particles were found to be useful for automatic dishwashing compositions.

An elegant method of microencapsulating active materials has been reported by Somerville and co-workers at the Southwest Research Institute. Key to this technology is a device with concentric feed tubes terminating in a rotary head. Active material, known as the filler, flows through the inner concentric tube while the coating material, known as the shell, flows through the outer concentric tube. As the head rotates, shell material emerges from the head and surrounds fill material continuously forming a series of individual capsules which break off. Descriptions of the process may be found in U.S. Pat. Nos. 3,015,128, 3,310,612 and 3,389,194. A summary of the process may be found in *Chemical Technology*, Oct. 1974, pp. 623–626 by Goodwin and Somerville entitled "Microencapsulation by Physical Methods".

Another method for obtaining microcapsules has been described in U.S. Pat. No. 3,943,063 (Morishita et al.). The method comprises the steps of dispersing or dissolving a core substance in a film-forming polymer solution. The dispersion or solution is emulsified into fine droplets in a vehicle which is poorly miscible with the polymer solution solvent and which does not dissolve the polymer. To the foregoing emulsion is added a non-solvent for the polymer, wherein the non-solvent is miscible with the solution solvent but poorly miscible with the vehicle, and does not dissolve the polymer.

These mutual solvent incompatibilities cause the polymer film to precipitate around the core substance.

Emulsion methods have also been discussed in U.S. Pat. No. 3,856,699 (Miyano et al.). The patent describes a process comprising dispersing core particles under heating into a waxy material, cooling the resultant dispersion, and crushing this into a powder. Thereafter, the powdered waxy material is agitated in an aqueous medium at a temperature higher than the melting point of the waxy material. Waxed core material is then passed into a non-agitated aqueous medium at a temperature lower than the melting point of the waxy material. A problem with this method is the extra processing steps involved in first having to prepare comminuted waxy material surrounding core particles.

U.S. Pat. No. 3,847,830 (Williams et al.) describes several methods for enveloping normally unstable peroxygen compounds in water dispersible coatings including that of paraffin waxes. Three of the methods require the enveloping agent to be molten hot prior to spraying onto the peroxygen particles held in a fluidised bed. Two other of the methods involve dissolving the enveloping agent in an organic solvent and either spraying the resultant solution onto the particles or immersing them in the bulk solution to achieve coating. Disadvantages of these two methods are the expense of organic solvents and, more importantly, the associated environmental pollution problems.

A process for encapsulating critical rubber and plastic chemicals has been disclosed in U.S. Pat. No. 4,092,285 (Leo et al.). Wax is heated to about 60°–150° C. along with other binder ingredients. Encapsulation is achieved by feeding heated binder into a high speed mixer containing the critical chemical in solid particulate form. Rapid mixing keeps the critical chemical particles separated so that every particle is discretely encapsulated rather than agglomerated during the mixing. The resultant particles are irregularly shaped. Further processing is required if regularly shaped particles are deemed desirable. Under circumstances where a binder component is a heat sensitive polymer, such as natural rubber or neoprene, a latex of the polymer is co-precipitated with an oil emulsion and this used as the binder system.

The present invention provides an alternative encapsulation method which provides certain advantages over those techniques known in the prior art. Thus, it is an object of the present invention to provide an encapsulation process which is free of organic solvents that lead to environmental pollution problems.

A further object of the invention is to provide a process resulting in encapsulated particles with a spherical and uniform coating substantially free of surface imperfections adversely affecting barrier properties in air or in a liquid medium.

A still further object of the invention is to provide a process which minimizes the need for expensive capital equipment and operates with a minimum of processing steps.

Another object of the invention is to provide capsules containing a core of one or more cleaning composition components including those of bleach, bleach precursors, enzymes, perfumes, fabric softeners and surfactants.

Finally, an object of the invention is to provide a liquid or solid cleaning composition containing the aforementioned encapsulated cleaning components. An even more specific object is to provide a dishwashing or other hard surface cleaner wherein chlorine or oxygen bleaches have been coated to prevent interaction with oxidation sensitive components such as enzymes, perfumes, fabric softeners and surfactants. Alternatively, the object encompasses a method wherein oxidation sensitive components are encapsulated to separate them from uncoated bleach.

These and other objects of the present invention will become apparent as further details are provided in the subsequent discussion and Examples.

SUMMARY OF THE INVENTION

A process for preparing particles of encapsulated active material is provided comprising:

(i) dispersing said active material in a melted wax to form an active material/wax dispersion;

(ii) adding said dispersion to water containing at least one surfactant and emulsifying the active material/-wax dispersion for no longer than 4 minutes therein to form capsules;

(iii) cooling immediately thereafter said capsules; and (iv) retrieving said cooled capsules from said water.

Improvement in capsule quality is further achieved by utilizing a blend of waxes wherein at least one wax has a different melting point from that of one or more further waxes. An annealing step is another improvement which reduces holes and cracks in the capsule coating. Annealing involves subjecting the cooled capsules to heat at an elevated temperature that is below the melting temperature of the wax mixture.

A further aspect of the invention is the provision of capsules comprising:

(i) a core of active material; and (ii) a coating on said core of a wax mixture having melting point 50° to 80° C. comprising a hard wax and a soft wax of needle penetration no higher than 30 mm and no lower than 35 mm, respectively, at 25° C., the ratio of hard to soft wax ranging between about 3:1 to 1:20 and the ratio of core to coating ranging between 10:1 to 1:10.

The invention also provides cleaning compositions containing the capsules. Of particular interest are dishwashing and other hard surface cleaning formulas containing wax encapsulated chlorine bleach in a system that may also contain one or more enzymes, perfumes, fabric softeners or surfactants. It is also possible to encapsulate the oxidation sensitive components to separate them from the bleach.

DETAILED DESCRIPTION OF THE INVENTION

The encapsulation process of this invention comprises four basic steps. These include: dispersing of the active in molten wax; emulsifying the active/wax dispersion in water; quenching of capsules by cooling; and retrieving solidified capsules, preferably by vacuum filtration.

Dispersion of actives in wax (homogenization) may be carried out using a high shear mixer. The wax temperature is controlled so that cooling to or below the melting point does not occur during addition of the active or during homogenization. Then, the resultant dispersion is emulsified into liquid droplets. Emulsification is accomplished by adding the dispersion to a stirred aqueous phase of distilled-deionized water and an emulsifying agent.

Quite important to the process is that the emulsification of active/dispersion in water be conducted for no longer than 4 minutes, preferably no longer than 2 minutes, optimally no longer than 60 seconds. The emulsification period is terminated by abrupt cooling of the aqueous active/wax dispersion system. Cooling is defined as reducing the temperature of the water emulsified dispersion, normally held above 55° C., to a temperature no higher than 50° C.

An important aspect of the process is the use of a surfactant, especially of the anionic or nonionic type, as emulsifying agent in the emulsification step. Absent surfactant, the active material-wax dispersion will not adequately distribute in the aqueous phase to form microcapsules. Normally, the surfactant will be present in an amount from about 0.001 to about 5% by weight of the aqueous phase, preferably from about 0.01 to about 1%, optimally between about 0.05 and 0.5%. Anionic surfactants are particularly useful and may broadly be described as compounds having one or more negatively charged functional groups, e.g. sulfonates or sulfates, attached to a hydrophobic moiety, e.g. fatty alkyl chain. Specific examples may be found in the section under "Surfactants" described in a latter part of this specification.

In the emulsification step, the temperature is controlled within a range of about 50° C. to about 100° C., preferably from about 60° C. to 85° C. A wide range of stirrer agitation speeds may be practiced and still obtain stable emulsions. Of course, particle size will vary with stirrer speed. Typical emulsification speeds may range from about 300 to 1200 rpm, depending on the quantity of material being emulsified, amount of foam, and the target capsule size.

Capsules are formed on cooling the aqueous phase either by direct addition of cold water or externally by chilling the reaction mixture; this is a critical step. Cooling is done as soon as the emulsion is formed. This minimizes loss of actives through diffusion. Formed capsules may be retrieved by vacuum filtration and washed thereafter with water to remove residual emulsifier.

The temperature of cold water used to quench the emulsification step and the rate of cooling can also be very important in forming smooth and even wax films. When cooling the encapsulated system, it is desirable to quench rapidly to avoid loss of actives to the aqueous phase. Water temperature should however not be so cold as to shock the crystallization of the wax coating. Moreover, it is important to quickly pass the congealing point of the wax mixture during quenching. This prevents agglomeration of the solidifying capsules in the last seconds of emulsification. It has been found that with wax blends having a melting point of approximately 70° C., cooling water of 10° C. results in a temperature drop to about 45°–47° C. This is sufficient to avoid agglomeration of the system that occurs in the temperature range from 60°–70° C. With systems exhibiting lower melting points, and hence lower processing temperatures, cooling may be carried out at a lower temperature.

Improved capsules are obtainable where blends of two or more waxes are utilized. Coatings resulting therefrom are more pliable and exhibit fewer surface defects.

Both a hard and a soft wax should be utilized for the mixture. The hard wax is characterized by a needle penetration no higher than 30 mm at 25° C., preferably no higher than 20 mm. The soft wax is characterized by a needle penetration no lower than 35 mm at 25° C., preferably no lower than 45 mm. The ratio of hard to soft wax should lie between about 3:1 to 1:20, preferably between 1:1 to 1:5, optimally between 1:1 and 1:2.

The Penetration Test (ASTM D 1321) is the standard industry test for hardness of waxes. The test measures the depth in tenths of a millimeter that a needle of a certain configuration under a given weight penetrates the surface of a wax at a given temperature.

Mixed waxes permit tailoring of the melting point. Thus, an approximate melting point of a wax mixture is given by the following relationship:

$$\text{Mixture Melting Point} = \frac{fa + f'b + f''c}{a + b + c}$$

where f=melting point of component A
f'=melting point of component B
f''=melting point of component C
a=parts of component A in mixture
b=parts of component B in mixture
c=parts of component C in mixture This relationship has been found to give a fair estimate of the midpoint of the melting range of the mixture. When mixtures are composed of components which differ greatly in melting point, the resultant mixture melting point tends to be broad, occasionally as much as a 10° C. range.

Another important criteria for the invention is that the mixture of waxes have a melting point ranging between 50° and 80° C., preferably between 55° and 70° C., optimally between 55° and 65° C.

A list of suitable hard waxes is provided in Table I. Suitable soft waxes are listed in Table II. These Tables also provide information on melting points and needle penetration values.

A number of wax additives may also be used. Pure linear hydrocarbons such as dodecane, octadecane and docosane are suitable wax additives. Esters may also be employed as additives with isopropyl myristate and isopropyl isostearate being preferred. Table III lists suitable wax-additive mixtures.

TABLE I

Hard Waxes

| Wax | Composition | Supplier | Melting Point (°C.) | Needle Penetration (mm) at 25° C. |
|---|---|---|---|---|
| Multiwax 110X (pale yellow) | microcrystalline | Witco | 55–60 | 19–23 |
| Duron 185J (pale yellow) | microcrystalline | Astor-Durachem | 80–82 | 15–20 |
| Duron Alof 180 (pale yellow) | microcrystalline | Astor-Durachem | 82–87 | 15–17 |
| Altafin 125/130 (white) | paraffin | Astor-Durachem | 51–54 | 13–17 |
| Altafin 135/140 (white) | paraffin | Astor-Durachem | 57–60 | 13–17 |
| Altafin 140/145 | paraffin | Astor-Durachem | 60–62 | 13–17 |
| Ross Wax 1329/1 (white) | microcrystalline | Frank B. Ross | 60–66 | 25–30 |
| Ross Wax 1365 (white) | microcrystalline | Frank B. | 60–66 | 25–30 |
| Refined Paraffin (white) | paraffin | Strahl & Pitsch | 51–54 | 9–15 |
| Epolene C16 (white) | polyethylene | Eastman Chemical | 106 | 3 |
| Bayberry (green) | natural bayberry wax | Frank B. Ross | 42–48 | 4–6 |
| Beeswax (white & yellow) | natural beeswax | Frank B. Ross | 62–65 | 15–20 |
| Candelilla (yellow) | natural candelilla | Frank B. Ross | 68–73 | 1.5–5 |
| Japan wax (yellow) | wax from berries of Japanese sumac | Frank B. Ross | 50–56 | 6–20 |
| Spermaceti substitute 573 (pale yellow) | synthetic spermaceti wax | Frank B. Ross | 42–50 | 10–14 |
| Be Square 175 (amber) | microcrystalline | Petrolite | 83.3 | 17 |
| Ultraflex | microcrystalline | Petrolite | 64.4 | 28 |

TABLE II

| Soft Waxes | | | | |
|---|---|---|---|---|
| Wax | Composition | Supplier | Melting Point (°C.) | Needle Penetration (mm) at 25° C. |
| Multiwax X145A (yellow) | microcrystalline | Witco | 66–71 | 35–45 |
| Multiwax W145A (white) | microcrystalline | Witco | 66–71 | 35–45 |
| Multiwax W-835 (white) | microcrystalline | Witco | 74–79 | 60–80 |
| Scale Paraffin (white) | paraffin — | Strahl & Pitsch | 50–53 | 25–43 |
| Multiwax B710 (white) | microcrystalline/ petrolatum | Witco | 60–66 | — |
| Petrolatum Snow (white) | petrolatum (microcrystalline & paraffin oil) | Penreco | 50–57 | — |

arts), bleach precursors, enzymes, perfumes, fabric softening agents, surfactants and mixtures thereof.

When the active material is an oxidizing material, it may be a chlorine or bromine releasing agent or a peroxygen compound. Among suitable reactive chlorine or bromine oxidizing materials are heterocyclic N-bromo and N-chloro imides such as trichloroisocyanuric, tribromoisocyanuric, dibromoisocyanuric and dichloroisocyanuric acids, and salts thereof with water-solubilizing cations such as potassium and sodium. Hydantoin compounds such as 1,3-dichloro-5,5-dimethylhydantoin are also quite suitable.

Dry, particulate, water-soluble anhydrous inorganic salts are likewise suitable for use herein such as lithium, sodium or calcium hypochlorite and hypobromite. Chlorinated trisodium phosphate is another core material. Chloroisocyanurates are, however, the preferred bleaching agents. Potassium dichloroisocyanurate is sold by the Monsanto Company as ACL-59®. Sodium dichloroisocyanurates are also available from Monsanto as ACL-60®, and in the dihydrate form, from the Olin Corporation as Clearon CDB-56®. Among the chloroisocyanurates the potassium salt ACL-59® provides better yields than ACL-60® or CDB-56®, due to its lower solubility in water.

TABLE III

| Wax | Wax Melting Point (°C.) | Ratio of Wax to Additive | Mixture Melting Point with Isopropyl Myristate Additive (°C.) | Mixture Melting Point with Isopropyl Isostearate Additive (°C.) | Mixture Melting Point with Dodecane Additive (°C.) | Mixture Melting Point with Octadecane Additive (°C.) |
|---|---|---|---|---|---|---|
| Bayberry | 41–49 | 90:10 | 39–47 | 39–46 | — | — |
| | | 75:25 | 38–47 | 38–47 | | |
| Yellow Beeswax | 56–63 | 90:10 | 53–61 | 53–62 | — | — |
| | | 75:25 | 54–62 | 56–64 | | |
| White Beeswax | 58–65 | 90:10 | 55–59 | 55–60 | — | — |
| | | 75:25 | 52–58 | 52–59 | | |
| Genuine Japan Wax | 46–55 | 90:10 | 44–53 | 42–53 | — | — |
| | | 75:25 | 40–47 | 43–54 | | |
| Multiwax 110X | 51–59 | 90:10 | 48–58 | 47–58 | 44–54 | 43–58 |
| | | 75:25 | 44–52 | 45–53 | 39–49 | 42–50 |
| Multiwax X145A | 62–72 | 90:10 | 58–64 | 57–64 | — | — |
| | | 75:25 | 58–64 | 57–62 | | |
| Refined Paraffin | 52–60 | 90:10 | 45–56 | 42–55 | 43–54 | 43–58 |
| | | 75:25 | 39–55 | 40–55 | 40–49 | 42–50 |
| Spermaceti Sub 573 | 42–54 | 90:10 | 39–47 | 39–48 | 40–45 | 40–45 |
| | | 75:25 | 40–48 | 37–48 | 37–42 | 38–43 |

Capsules of the invention will have a core of active material surrounded by a coating of wax. The ratio of core to coating will range between 2:1 to 1:20, preferably between 1:1 to 1:10, optimally about 1:3.

Annealing of capsules has been found to be extremely useful in improving integrity of the coating. By annealing, it is meant that the capsules are held at an elevated temperature, but one that is below the wax melting point, for a period in excess of about one hour. Most preferably, annealing should be performed for a period between 1 and 48 hours, optimally between about 4 and 24 hours. Mixing the capsules with an inert material, such as amorphous silica, alumina or clay, prevents capsule sticking during the annealing process. Incorporation of the inorganic annealing adjunct allows use of higher temperatures during the annealing process, thus shortening the annealing period. Adjuncts may be used in an amount relative to the weight of the overall capsule in the ratio of 1:200 to 1:20, preferably about 1:100.

Active Materials

1. Bleach

Active materials may include those chosen from oxidizing materials (known as bleaches in the cleaning Organic peroxy acids may be utilized as the active material within the opaque particle. The peroxy acids usable in the present invention are solid and, preferably, substantially water-insoluble compounds. By "substantially water-insoluble" is meant herein a water-solubility of less than about 1% by weight at ambient temperature. In general, peroxy acids containing at least about 7 carbon atoms are sufficiently insoluble in water for use herein.

Typical monoperoxy acids useful herein include alkyl peroxy acids and aryl peroxy acids such as:

(i) peroxybenzoic acid and ring-substituted peroxybenzoic acids, e.g. peroxy-α-naphthoic acid
(ii) aliphatic and substituted aliphatic monoperoxy acids, e.g. peroxylauric acid and peroxystearic acid.

Typical diperoxy acids useful herein include alkyl diperoxy acids and aryldiperoxy acids, such as:

(iii) 1,12-diperoxydodecanedioic acid
(iv) 1,9-diperoxyazelaic acid
(v) diperoxybrassylic acid; diperoxysebacic acid and diperoxyisophthalic acid
(vi) 2-decyldiperoxybutane-1,4-dioic acid.

Inorganic peroxygen generating compounds may also be suitable as cores for the particles of the present invention. Examples of these materials are salts of monopersulfate, perborate monohydrate, perborate tetrahydrate, and percarbonate.

2. Bleach Precursors

Solid bleach precursors or activators may also be usefully coated by the process of the present invention. Illustrative of organic precursors are N,N,N',N'-tetraacetyl-ethylene diamine (TAED), benzoyloxybenzene sulfonate and sodium nonanoyloxybenzene sulfonate. Inorganic bleach catalysts such as manganese salts or manganese ions adsorbed onto aluminosilicate supporting substrates such as zeolites could also benefit from this invention. The manganese catalysts may be prepared according to the method primarily described in U.S. Pat. No. 4,536,183 (Namnath). Other catalysts of this type are more fully described in U.S. Pat. No. 4,601,845 (Namnath), U.S. Pat. No. 4,626,373 (Finch et al.) and U.S. Pat. No. 4,728,455 (Rerek).

3. Enzymes and Perfumes

Enzymes and perfumes may be used as the active materials. These enzymes and perfumes may be deposited or entrapped upon a supporting substrate such as an inorganic salt, aluminosilicate, organic polymer or other non-interactive solid base material. Suitable enzymes include those classed under lipase, protease, cellulase and amylase. Particularly preferred is the protease known as Savinase® and the amylase known as Termanyl®.

4. Fabric Softeners

Fabric softening agents are a further category of active materials suitable for this invention. These materials are defined as cationic compounds having at least one long chain alkyl group of about 10 to 24 carbon atoms. See "Cationic Surfactants", Jungermann, 1970, herein incorporated by reference. These quaternary compounds may be selected from:

(i) non-cyclic quaternary ammonium salts of the formula:

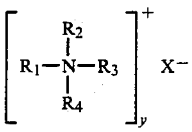

wherein $R_1$ is an alkyl or alkenyl group having from 8 to 22 carbon atoms; $R_2$ is an alkyl group containing from 1 to 3 carbon atoms; $R_3$ and $R_4$ is selected from the group consisting of $R_1$ and $R_2$; X is an anion selected from the group consisting of halides, sulfates, alkyl sulfates having from 1 to 3 carbon atoms in the alkyl chain, and acetates; and y is the valency of X.

The instant class of quaternaries is preferred above other similar types. Particularly preferred is dimethyl dihydrogenated tallow ammonium chloride. This fabric softener is sold as Adogen 442® by the Sherex Corporation.

(ii) substituted polyamine salts of the formula:

(I)

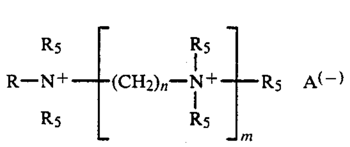

wherein R is an alkyl or alkenyl group having 10 to 22 carbon atoms, the $R_5$'s which may be the same or different each represent hydrogen, a $(C_2H_4O)_pH$ or $(C_3H_6O)_qH$, or a $C_{1-3}$ alkyl group, where each of p and q is a number such that $(p+q)$ does not exceed 25, m is from 1 to 9, n is from 2 to 6, and $A(-)$ represents one or more anions having total charge balancing that of the nitrogen atoms;

(iii) polyamine salts having the formula I where R is hydrogen or a $C_{1-4}$ alkyl group, n is from 2 to 6 and m is not less than 3;

(iv) $C_{8-25}$ alkyl imidazolinium salts; and (v) $C_{12-20}$ alkyl pyridinium salts.

Alkyl imidazolinium salts of class (iv) useful in the present invention are generally believed to have cations of the formula:

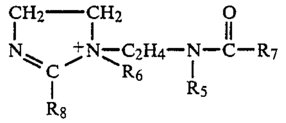

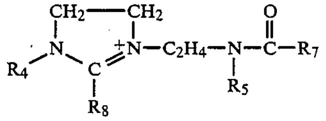

where $R_5$ is hydrogen or a $C_1$–$C_4$ alkyl radical, $R_6$ is a $C_1$–$C_4$ alkyl radical, $R_7$ is a $C_9$–$C_{25}$ alkyl radical and $R_8$ is hydrogen or a $C_8$–$C_{25}$ alkyl radical.

A preferred member of this class is believed to have $R_6$ methyl and $R_7$ and $R_8$ tallow alkyl, $R_5$ hydrogen, and is marketed under the trademark Varisoft 475 by the Sherex Chemical Company.

5. Surfactants

Surfactants may be protected as an active material. Useful surfactants include anionic, nonionic, cationic, amphoteric, zwitterionic types and mixtures of these surface active agents. Such surfactants are well known in the detergent art and are described at length in "Surface Active Agents and Detergents", Vol. II, by Schwartz, Perry & Birch, Interscience Publishers, Inc. 1958, herein incorporated by reference.

Anionic synthetic detergents can be broadly described as surface active compounds with one or more negatively charged functional groups. Soaps are included within this category. A soap is a $C_8$–$C_{22}$ alkyl fatty acid salt of an alkali metal, alkaline earth metal, ammonium, alkyl substituted ammonium or alkanolammonium salt. Sodium salts of tallow and coconut fatty acids and mixtures thereof are most common. Another important class of anionic compounds are the water-soluble salts, particularly the alkali metal salts, of organic sulfur reaction products having in their molecular structure an alkyl radical containing from about 8 to 22 carbon atoms and a radical selected from the group consisting of sulfonic acid and sulfuric acid ester radicals. Organic sulfur based anionic surfactants include the salts of $C_{10}$–$C_{16}$ alkylbenzene sulfonates, $C_{10}$–$C_{22}$ alkane sulfonates, $C_{10}$–$C_{22}$ alkyl ether sulfates, $C_{10}$–$C_{22}$ alkyl sulfates, $C_4$–$C_{10}$ dialkylsulfosuccinates, $C_{10}$–$C_{22}$ acyl isethionates, alkyl diphenyloxide sulfonates, alkyl naphthalene sulfonates, and 2-acetamido hexadecane sulfonates. Also included are nonionic alkoxylates having a sodium alkylene carboxylate moiety linked to a terminal hydroxyl group of the nonionic through an ether bond.

Counterions to the salts of all the foregoing may be those of alkali metal, alkaline earth metal, ammonium, alkanolammonium and alkylammonium types.

Nonionic surfactants can be broadly defined as compounds produced by the condensation of alkylene oxide groups with an organic hydrophobic material which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements. Illustrative, but not limiting examples, of various suitable nonionic surfactant types are:

(a) polyoxyethylene or polyoxypropylene condensates of aliphatic carboxylic acids, whether linear- or branched-chain and unsaturated or saturated, containing from about 8 to about 18 carbon atoms in the aliphatic chain and incorporating from 5 to about 50 ethylene oxide and/or propylene oxide units. Suitable carboxylic acids include "coconut" fatty acids (derived from coconut oil) which contain an average of about 12 carbon atoms, "tallow" fatty acids (derived from tallow-class fats) which contain an average of about 18 carbon atoms, palmitic acid, myristic acid, stearic acid and lauric acid.

(b) polyoxyethylene or polyoxypropylene condensates of aliphatic alcohols, whether linear- or branched-chain and unsaturated or saturated, containing from about 6 to about 24 carbon atoms and incorporating from about 5 to about 50 ethylene oxide and/or propylene oxide units. Suitable alcohols include "coconut" fatty alcohol, "tallow" fatty alcohol, lauryl alcohol, myristyl alcohol and oleyl alcohol. Particularly preferred nonionic surfactant compounds in this category are the "Neodol" type products, a registered trademark of the Shell Chemical Company.

Also included within this category are nonionic surfactants having the formula:

$$R-(CH_2\underset{\displaystyle R'}{\underset{|}{C}}HO)_x(CH_2CH_2O)_y(CH_2\underset{\displaystyle R''}{\underset{|}{C}}HO)_z-H$$

wherein R is a linear alkyl hydrocarbon having an average of 6 to 10 carbon atoms, R' and R" are each linear alkyl hydrocarbons of about 1 to 4 carbon atoms, x is an integer from 1 to 6, y is an integer from 4 to 15 and z is an integer from 4 to 25. A particularly prefered example of this category is Poly-Tergent SLF-18, a registered trademark of the Olin Corporation, New Haven, Conn. Poly-Tergent SLF-18 has a composition of the above formula where R is a $C_6$–$C_{10}$ linear alkyl mixture, R' and R" are methyl, x averages 3, y averages 12 and z averages 16.

(c) polyoxyethylene or polyoxypropylene condensates of alkyl phenols, whether linear- or branched-chain and unsaturated or saturated, containing from about 6 to about 12 carbon atoms and incorporating from about 5 to about 25 moles of ethylene oxide and/or propylene oxide.

(d) polyoxyethylene derivatives of sorbitan mono-, di-, and tri-fatty acid esters wherein the fatty acid component has between 12 and 24 carbon atoms. The preferred polyoxyethylene derivatives are of sorbitan monolaurate, sorbitan trilaurate, sorbitan monopalmitate, sorbitan tripalmitate, sorbitan monostearate, sorbitan monoisostearate, sorbitan tristearate, sorbitan monooleate, and sorbitan trioleate. The polyoxyethylene chains may contain between about 4 and 30 ethylene oxide units, preferably about 20. The sorbitan ester derivatives contain 1, 2 or 3 polyoxyethylene chains dependent upon whether they are mono-, di- or tri-acid esters.

(e) polyoxyethylene-polyoxypropylene block copolymers having the formula:

$$HO(CH_2CH_2O)_a(CH(CH_3)CH_2O)_b(CH_2CH_2O)_cH$$

wherein a, b and c are integers reflecting the respective polyethylene oxide and polypropylene oxide blocks of said polymer. The polyoxyethylene component of the block polymer constitutes at least about 40% of the block polymer. The material preferably has a molecular weight of between about 2,000 and 10,000, more preferably from about 3,000 to about 6,000. These materials are well known in the art. They are available under the trademark "Pluronics", a product of BASF-Wyandotte Corporation.

Amphoteric synthetic detergents can be broadly described as derivatives of aliphatic and tertiary amines, in which the aliphatic radical may be straight chain or branched and wherein one of the aliphatic substituents contain from about 8 to about 18 carbons and one contains an anionic water-solubilizing group, i.e. carboxy, sulpho, sulphato, phosphato or phosphono. Examples of compounds falling within this definition are sodium 3-dodecylamino propionate and sodium 2-dodecylamino propane sulfonate.

Zwitterionic synthetic detergents can be broadly described as derivatives of aliphatic quaternary ammonium, phosphonium and sulphonium compounds in which the aliphatic radical may be straight chained or branched, and wherein one of the aliphatic substituents contains from about 8 to about 18 carbon atoms and one contains an anionic water-solubilizing group, e.g. carboxy, sulpho, sulphato, phosphato or phosphono. These compounds are frequently referred to as betaines. Besides alkyl betaines, alkyl amino and alkyl amido betaines are encompassed within this invention. Cocoamido-propyl dimethyl betaine is a particularly useful surfactant.

Encapsulation of a surfactant is an inherently difficult task. Surfactant molecules orient themselves at the interface between the "water" and "oil" phases thus defeating the objective of the encapsulation process. For instance, it has been observed that during processing the surfactants diffuse out of the internal wax-surfactant dispersion to the external aqueous phase.

Improved retention of surfactant dispersed in the wax phase and higher encapsulation yields can be achieved through selection of a wax that permits solubilization of the surfactant in the molten wax and by reducing the time for emulsification. For definition purposes, solubilization is considered to be a form of dispersal. Solubilizing wax phases can be obtained by using additives to modify melting point and polarity of the wax compounds. Wax-additive mixtures and their melting points have been given in Table III above. For instance, dissolution of the wax-surfactant composition, followed by examination of the resulting film under an optical microscope, revealed that Tergitol Min Foam 2X dissolved in Multiwax 110X, refined paraffin wax, Spermaceti substitute, bayberry wax and Genuine Japanese wax. By contrast, Polytergent SLF-18 dissolved only in Spermaceti substitute, bayberry wax and Genuine Japan wax. The Alfonic solid nonionic surfactants were found to dissolve in Multiwax 110X, refined paraffin wax and Spermaceti substitute.

Liquid nonionic surfactants have been encapsulated at levels from 0.5 up to 40% of the total capsule weight based on initial surfactant concentration of 50%, i.e. actual 80% retention of nonionic surfactant in the capsules.

The content of nonionic surfactant in the capsules may be maximized through rapid quenching of the emulsified mixture. Rapid quenching may be performed by surrounding the reaction vessel with an ice water jacket. Quenching is carried out as soon as the emulsion has formed in order to limit diffusion of surfactant to the oil-water interface. Direct internal cooling by addition of cold water to the reaction mixture may also be suitable.

Active material capsules of the present invention may be incorporated into a variety of cleaning compositions. These compositions include fabric washing, fabric softening, automatic machine dishwashing, light duty dishwashing and hard surface cleaning powder and liquid compositions. Most of these compositions will contain from about 0.001 to 5% of a perfume component. Certain of the foregoing type of products will also contain from about 0.01 to about 15% of a surfactant, preferably about 0.5% to about 10% by weight of the composition.

Most especially, the present invention is directed to a process for encapsulating a chlorine bleach active which is to be utilized in an automatic dishwashing detergent composition. Capsules will be present in these compositions in an amount sufficient to release at least about 0.1% by weight available chlorine based on the total composition. Automatic dishwashing detergent powders and liquids will have the composition listed in Table IV.

TABLE IV

Automatic Dishwashing Detergent Compositions

| Components | Powder Formulation (Percent by Weight) | Liquid Formulation (Percent by Weight) |
|---|---|---|
| Builder | 5–70 | 10–60 |
| Nonionic Surfactant | 1–15 | 0.01–2 |
| Silicate | 1–20 | 5–20 |
| Filler | 0–60 | — |
| Bleaching Agent | 0.1–20 | 0.1–20 |
| Clay | 0–5 | 0–5 |
| Perfume | 0.001–5 | 0.001–5 |
| Water | till 100 | till 100 |

The following examples will more fully illustrate the embodiments of the invention. All parts, percentages and proportions referred to herein and in the appended claims are by weight unless otherwise indicated.

EXAMPLE 1

The following Example illustrates preparation of chlorine bleach actives coated with a wax composition. From 5 to 9 grams of ACL-59 ® were dispersed in 12 grams of a molten wax blend. A Tekmar Tissumizer apparatus fitted with an SDT-182E probe operated at high shear for two minutes was used to perform the dispersion step. The internal temperature of the wax mixture was maintained at 55° C. so that cooling to or below the wax melting point did not occur when the active was added or during the dispersion or homogenization.

Thereafter, an emulsification step was performed in a 600 ml beaker containing an aqueous phase whereinto was added the ACL-59 ®-wax composition. The aqueous phase consisted of about 200 grams distilled-deionized water and 0.5% Dowfax 2A1 ® surfactant. The level of surfactant was adjusted with each system to achieve optimal capsule size and morphology.

For the emulsification step, borosilicate glass stirring shafts were used with a Teflon stirrer blade. The aqueous phase was maintained at about 60° C. using a thermostated hotplate to control the temperature of the water bath surrounding the reactor beaker. Stirrer speed was 340 rpm. Emulsification speeds were varied from 300 to 1200 rpm, depending on the quantity of material being emulsified, amount of foam, and the desired capsule size.

Capsules were solidified on cooling the aqueous phase by addition of 200 ml water of 10° C. temperature. Alternative to the direct addition of cold water is the method of externally chilling the reaction mixture using an ice jacket. Cooling was done as soon as the emulsion formed in order to minimize loss of actives through diffusion. The formed capsules were then retrieved by vacuum filtration and washed with water to remove residual emulsifier.

Capsule stability was further improved by an annealing step. Therein, the capsules were mixed with 1% amorphous silica to prevent sticking and then placed in an oven at 40° C. for a period of 24 hours. During the annealing, the wax coating softened slightly and moved sufficiently to close large pores and cracks on the capsule surface.

Emulsification times can be important for improving the level of encapsulated bleach. For instance, capsule chlorine content improved when rapid, internal quenching was applied after 30 seconds to stop emulsification. Improvement in capsule chlorine content was thereby increased from 5 to 70% available chlorine based on total capsule weight. Chlorine loss directly corresponded to the increased emulsification times.

TABLE V

Chlorine Loss as a Function of Emulsification Times

| Emulsification Time (min.) | Percent Chlorine Loss to Aqueous Phase |
|---|---|
| 1 | 24.5 |
| 2 | 68.1 |
| 4 | 83.8 |

A fourfold scale-up of the encapsulated system was achieved producing 50–55 grams of capsules, with an average yield of 80%. The capsules prepared in this scale-up show the same high chlorine content, size distribution and low chlorine release in water as those prepared in the small batch.

Screening of Capsule Stability

Mechanical Test

Chlorine bleach capsules were evaluated for stability by determining the amount of chlorine released from the capsules in water, in the presence of potassium iodide and acetic acid, with gentle stirring for 20 minutes. This was done by standard iodometric titration without the use of chloroform or other organic solvents that may dissolve the wax coating.

The mechanical test is a reliable indication of how well the capsules will perform in liquid automatic dishwashing detergents (ADD) formulations. It has been found that most capsules which release less than one percent of the total available chlorine demonstrate good storage stability at 40° C. in a liquid ADD formulation.

SEM

Scanning electron micrographs taken at low accelerating voltages were used to ascertain the presence of capsule surface defects such as cracks or holes which are responsible for low capsule stability, under product storage conditions.

The capsules were prepared for SEM analysis by forming a cross-section of the substrate under a steromicroscope, followed by coating with a thin layer of gold under argon atmosphere. Prepared SEM samples were examined using a JEOL T300 SEM operated at 5 kV accelerating voltage.

EXAMPLE 2

The following work investigated the various types of chlorine bleaches using the method described by Example 1. Capsules were prepared with the following solid chlorine bleaches: ACL-59®, ACL-60®, CDB-56® and 1,3-dichloro-5,5-dimethyl hydantoin. A critical factor in preparing capsules of good performance appeared to be the form of the bleach. Finely ground, small particulate powders were best suspended in the wax system during homogenization and emulsification, resulting in the highest yields. Of these four bleaches, ACL-60® and CDB-56® gave relatively poor capsules, probably for the reason that they were not in fine powder form. Of the remaining two bleaches, encapsulation was more successful with the ACL-59®.

A further batch of capsules were prepared with ACL-59® in 90% microcrystalline wax and 10% polyethylene wax with high chlorine levels (18–20% available chlorine). These capsules demonstrated good chlorine stability under both mechanical test conditions and storage stability in a liquid ADD at 40° C. Capsule size ranged from 500–1200 microns, with an average size of approximately 700 microns. These capsules were hard, exhibiting an average compression strength of 0.763N, as measured by an Instron Universal Instrument. The capsules melted from 67°–78° C., and compared favorably under storage conditions with samples prepared by the method of Somerville mentioned above.

EXAMPLE 3

A number of experiments are herein described evaluating criticalities associated with use of a mixture of hard and soft waxes. Different wax combinations were used to encapsulate ACL-59® chlorine bleach particles. The resultant capsules were then subjected to the mechanical test described in Example 1. Table VI illustrates the wax compositions and percent chlorine diffused. The higher the amount of chlorine detected, the higher was diffusion through the holes and cracks of the capsules.

TABLE VI

| Composition | % Chlorine Diffused |
|---|---|
| 100% Multiwax 110-X | 8.7 |
| 75% Multiwax 110-X/25% Multiwax X 145 A | 6.5 |
| 50% Multiwax 110-X/50% Multiwax X 145 A | 2.0 |
| 25% Multiwax 110-X/75% Multiwax X 145 A | 1.1 |
| 100% Multiwax X 145 A | 1.3 |

Multiwax 110-X is a hard wax (needle penetration=19–25 mm at 25° C.) and Multiwax X 145 A is a softer wax (needle penetration=35–45 mm at 25° C.). A relatively large amount of chlorine diffused from capsules coated only with Multiwax 110-X. Much lower diffusion was observed with a 3:1 mixture of hard to soft wax. Especially effective were 1:1 or lower ratio mixtures of hard to soft wax.

Table VII reports combinations of Duron 185 J which is a hard wax (needle penetration=15–20 mm at 25° C.) with Snow Petrolatum which is a very soft wax composed of a microcrystalline wax and about 10% paraffin oil. From the results listed in Table VII, it is evident that the hard wax must be mixed with softer wax to obtain low chlorine diffusion.

TABLE VII

| Composition | % Chlorine Diffused |
|---|---|
| 90% Duron 185 J/10% Snow Petrolatum | 4.2 |
| 80% Duron 185 J/20% Snow Petrolatum | 3.0 |
| 75% Duron 185 J/25% Snow Petrolatum | 1.7 |

Table VIII illustrates the effect of using a third wax component to reduce the diffusion from the capsules. Multiwax W-835 was employed as the third wax in combination with Duron Alof 180 and Epolene C16.

TABLE VIII

| Composition | % Chlorine Diffused |
|---|---|
| 90% Multiwax W-835/10% Epolene C16 | 3.6 |
| 70% Multiwax W-835/20% Duron Alof 180/ 10% Epolene C16 | 2.1 |
| 45% Multiwax W-835/45% Duron Alof 180/ 10% Epolene C16 | 1.3 |

EXAMPLE 4

This Example demonstrates the importance of selecting a wax mixture that exhibits a melting point between 50° and 80° C. Table IX profiles the chlorine release values of three samples tested in a Kenmore dishwasher. The first is uncoated ACL-59® bleach particles, the second is ACL-59® encapsulated in a wax mixture of 90% Duron Alof 180 and 10% Epolene, the melting point of which is 72°–83° C. A third sample tested was ACL-59® encapsulated in a wax mixture of 90% Multiwax X-145A and 10% Epolene which combination had a melting point of 67°–78° C.

TABLE IX

| | % Chlorine Released | | |
|---|---|---|---|
| Time (Minutes) | Unencapsulated ACL-59 ® | Duron/Epolene Capsulated ACL-59 ® | Multiwax/Epolene Capsulated ACL-59 ® |
| 6 | 47 | 10 | 33 |
| 8 | 74 | 9 | 43 |
| 10 | 74 | 13 | 51 |
| 12 | 74 | 12 | 51 |
| 14 | 74 | 14 | 57 |

From the results listed in Table IX, it appears that the higher melting point wax encapsulated particles provided slower release of chlorine.

EXAMPLE 5

The following procedure illustrates the encapsulation of nonionic surfactants such as Min-Foam 2X. Nine grams spermaceti Sub 573 were heated to the melt temperature and vigorously stirred. Into this wax were added 10 grams Min-Foam 2X and 1.0 gram isopropyl myristate. Thereafter, the dispersed Min-Foam 2X/wax mixture was rapidly added to an aqueous phase comprising 200 grams distilled deionized water containing 0.167 grams Dowfax 2A1 ®. The emulsion at 60° C. was homogenized for 1.5 minutes at 400 rpm. Microcapsules resulting from the foregoing emulsification were then separated by vacuum filtration.

EXAMPLE 6

This Example provides a further illustration of encapsulating a nonionic surfactant in a wax mixture. Five grams of SLF-18 surfactant was added to 10 grams molten mixture of Multiwax X-145A and Epolene C16. The resultant dispersion was then added to 200 grams of deionized water containing 1 gram of Dowfax 2A-1 ®. The emulsion was homogenized for 30 seconds at 600 rpm and thereafter quenched by the addition of 10° C. water. Capsules formed therefrom were separated by vacuum filtration. Colorimetric analysis for the nonionic surfactant indicated greater than 85–90% retention within the capsule.

EXAMPLE 7

The following series of experiments show the importance of limiting emulsification time of the active material/wax dispersion in water. Table X reports the amount of active material remaining within the capsule under various emulsification times.

TABLE X

Quenching Times

I. Encapsulation of ACL-59 ® in 90/10 Multiwax W-145 and Epolene C-16

| Time (sec.) | % Chlorine in Capsules |
|---|---|
| 15 | 69.5 |
| 30 | 66.9 |
| 60 | 76.6 |
| 120 | 71.1 |
| 240 | 60.3 |

II. Encapsulation of Calcium Hypochlorite in 100% Multiwax X-100

| Time (sec.) | % Chlorine in Capsules |
|---|---|
| 15 | 29.1 |
| 30 | 30.2 |
| 60 | 26.5 |
| 120 | 18.9 |
| 240 | 15.5 |

III. Encapsulation of Calcium Hypochlorite in 90/10 Multiwax W-145 and Epolene C16

| Time (sec.) | % Chlorine in Capsules |
|---|---|
| 15 | 47.6 |
| 240 | 32.6 |

IV. Encapsulation of SLF-18 in 90/10 Multiwax W-145 and Epolene C16

| Time (sec.) | % Nonionic in Capsule |
|---|---|
| 15 | 30.8 |
| 30 | 37.2 |
| 60 | 20.7 |
| 120 | 10.0 |
| 240 | 8.3 |

From the percent retention of active materials in the above Table, it appears that 240 seconds should be the maximum time for the emulsification prior to quenching. Preferably, quenching should occur within the first 60 seconds of the emulsification period.

EXAMPLE 8

This Example illustrates the use and performance of microcapsules prepared by the method of this invention in automatic dishwashing detergent formulations. Detailed below are the base formulas of a typical clay-thickened and a clear gel type automatic dishwashing formulation.

TABLE XI

| Compound | % in Formulation |
|---|---|
| A. Clay-Thickened Formula | |
| Sodium tripolyphosphate (anhydrous) | 11.54 |
| Sodium tripolyphosphate (hexahydrate) | 9.36 |
| Sodium carbonate | 7.00 |
| Sodium silicate (R = 2.4) | 6.40 |
| Dowfax 3B2 (anionic emulsifier) | 0.40 |
| Sodium hypochlorite (ave. chlorine) | 1.00 |
| Monostearyl acid phosphate | 0.16 |
| Sodium hydroxide | 1.20 |
| Bentonite | 3.00 |
| Water | balance to 100 |
| B. Clear Gel Formula | |
| Tetrapotassium polyphosphate | 19.00 |
| Britesil H20 | 7.50 |
| Potassium carbonate | 6.00 |
| Sodium tripolyphosphate | 1.00 |
| Polytergent SLF-18 ® | 1.00 |
| Encapsulated Chlorine Bleach | 5.00 |
| Potassium hydroxide | 1.00 |
| Catapal D Alumina | 0.10 |
| Carbopol 941 ® | 1.00 |
| Water | balance to 100 |

Storage stability of the nonionic encapsulates were evaluated at 40° C. in the above-identified clay-thickened base formula.

TABLE XII

Storage Stability Testing of Nonionic Encapsulates in Clay-Thickened ADD at 40° C.

| Sample | % Avail. Chlorine Initially | After 1 week |
|---|---|---|
| 1 | 0.843 | 0.128 |
| 2 | 0.864 | 0.137 |
| 3 | 0.8340 | 0.0537 |
| 4 | 0.778 | 0.130 |

Sample 1: Min-Foam 2X in 90/10 Spermaceti sub 573/isopropyl myristate
Sample 2: Min-Foam 2X in 90/10 Spermaceti sub 573/isopropyl myristate
Sample 3: Polytergent SLF-18 in 90/10 Spermaceti sub 573/dodecane
Sample 4: Polytergent SLF-18 in 90/10 Spermaceti sub 573/isopropyl myristate

EXAMPLE 9

The following experiments illustrate the performance of the chlorine encapsulated bleach particles as prepared by the method of Example 1. The chlorine bleach encapsulates were evaluated in a clay-thickened automatic dishwashing liquid whose base formula is provided in Example 8. Table XIII below outlines the effect of using various different types of waxes. It is clear from the Table that the best storage stabilities of chlorine bleach are obtained through the use of refined paraffin.

TABLE XIII

| Storage Stabilities of Chlorine Bleach in Various Waxes in Clay-Thickened Automatic Dishwashing Liquids at 40° C. | | | | | |
|---|---|---|---|---|---|
| Wax Sample | Initially | 1 Week | 2 Weeks | 3 Weeks | 4 Weeks |
| Refined Paraffin | 100 | 100 | 73.8 | 82.1 | 84.0 |
| Multiwax 110X | 100 | 91.5 | 82.9 | 65.8 | 64.0 |
| Candelilla | 100 | 68.2 | 35.4 | 8.0 | 4.8 |
| Spermaceti sub 573 | 100 | 57.7 | 24.1 | 10.3 | 4.0 |

EXAMPLE 10

The following experiments compare the chlorine bleach storage stability of microcapsules made by the present method relative to those microcapsules made by the method of Somerville. The stability was followed by measuring the chlorine release at 40° C. in an automatic dishwashing gel formulation as outlined in Table XI(B). Sample 1 was made according to Example 1 of the present specification. Sample 2 was made according to the method of Somerville. From Table XIV, it is seen that microcapsules prepared by the present invention (Sample 1) had a clearly slower chlorine release profile, indicating that the capsules were more stable under storage conditions.

TABLE XIV

| Storage Stability Testing of Encapsulates in Gel ADD at 40° C. | | |
|---|---|---|
| | % Chlorine Remaining | |
| Time (weeks) | Sample 1 | Sample 2 |
| 0 | 100.0 | 100.0 |
| 1 | 100.0 | 100.0 |
| 2 | 87.0 | 100.0 |
| 3 | 82.0 | 47.0 |
| 4 | 55.0 | 29.0 |
| 5 | 39.1 | 26.8 |
| 6 | 73.9 | 27.8 |
| 7 | 21.7 | 14.4 |

The foregoing description and Examples illustrate selected embodiments of the present invention. In light thereof, various modifications will be suggested to one skilled in the art, all of which are within the spirit and purview of this invention.

What is claimed is:

1. A process for preparing particles of encapsulated active material comprising:
   (i) selecting a mixture of waxes wherein one wax of said mixture has a melting point different from another of said waxes, said mixture having a melting point between 50°-80° C., and melting said mixture to obtain a melted wax;
   (ii) dispersing said active material in said melted wax to form an active material/wax dispersion, said active material being selected from the group consisting of chlorine or oxygen bleaching agents and bleach precursors;
   (iii) adding said dispersion to water containing at least one surfactant and emulsifying the active material/wax dispersion for no longer than 4 minutes therein to form capsules;
   (iv) cooling immediately thereafter said capsules;
   (v) retrieving said cooled capsules from said water; and
   (vi) annealing said retrieved capsules for a period between 4 and 24 hours.

2. A process according to claim 1 wherein said active material is a chlorine releasing bleach.

3. A process according to claim 2 wherein said chlorine releasing bleach is an alkali metal salt of dichloroisocyanurate.

4. A process according to claim 1 wherein said active material is an oxygen bleaching agent.

5. A process according to claim 4 wherein said oxygen bleaching agent is selected from the group consisting of 1,12-diperoxydodecanedioic acid, sodium perborate monohydrate and sodium perborate tetrahydrate.

6. A process according to claim 1 wherein the active material is a bleach precursor.

7. A process according to claim 6 wherein the bleach precursor is selected from the group consisting of N,N,N',N'-tetraacetyl-ethylene diamine, benzoyloxybenzene sulfonate, and sodium nonanoyloxybenzene sulfonate.

8. A process according to claim 1 wherein an inert mineral selected from amorphous silica, alumina, clay and mixtures thereof, is contacted with the capsules in an amount sufficient to prevent sticking during the annealing step.

9. A process according to claim 1 wherein the emulsifying step is for no longer than 60 seconds.

* * * * *